United States Patent [19]
Takeo et al.

[11] Patent Number: 5,955,505
[45] Date of Patent: *Sep. 21, 1999

[54] GLUTAMIC ACID RECEPTOR AGONIST

[75] Inventors: Jiro Takeo; Shinya Yamashita; Keiji Wada; Yoshiyuki Chiba, all of Tokyo, Japan

[73] Assignee: Nippon Suisan Kaisha, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/894,433

[22] PCT Filed: Feb. 20, 1996

[86] PCT No.: PCT/JP96/00379

§ 371 Date: Aug. 20, 1997

§ 102(e) Date: Aug. 20, 1997

[87] PCT Pub. No.: WO96/25926

PCT Pub. Date: Aug. 29, 1996

[30] Foreign Application Priority Data

Feb. 21, 1995 [JP] Japan ............................... 7-170357

[51] Int. Cl.$^6$ ........................... A61K 31/18; A61K 31/44
[52] U.S. Cl. .......................... 514/604; 514/347; 514/534; 514/540; 514/562; 514/602; 514/603; 514/605; 546/293; 560/9; 560/12; 560/13; 562/434; 562/435; 562/437; 562/438; 562/442; 562/451; 564/86; 564/87; 564/89; 564/90
[58] Field of Search ................... 564/86, 87, 89, 564/90, 91, 92, 99; 560/9, 12, 13; 562/434, 435, 437, 438, 442, 451; 514/534, 540, 562, 602, 603, 604, 605

[56] References Cited

U.S. PATENT DOCUMENTS

| | | | |
|---|---|---|---|
| 4,369,139 | 1/1983 | Kyburz et al. | 548/539 |
| 4,990,511 | 2/1991 | Nakajima et al. | 514/255 |
| 5,189,211 | 2/1993 | Sato et al. | 562/430 |
| 5,677,330 | 10/1997 | Abraham et al. | 514/421 |

FOREIGN PATENT DOCUMENTS

WO 97/07799 3/1997 WIPO .

OTHER PUBLICATIONS

AMPA Receptor Heterogeneity in Rat Hippocampal Neurons Revealed by Differential Sensitivity to Cyclothiazide : Fleck, Mark W. et al. ; Journal of Neurophirosiology vol. 75, No. 6 Jun. 1996 pp. 2322–2333.

Cyclothiazide Modulates AMPA Receptor–Mediated Increases in Intracellular Free $Ca^{2+}$ and $Mg^{2+}$ in Cultured Neurons From Rat Brain : Hyot Kari R. et al. ; Journal of Neurochemistry vol. 64, No. 5, 1995 pp. 2049–2056.

Cyclothiazide Differentially Modulates Desensitization of α–Amino–3–hydroxy–5–methyl–4–isoxazolepropionic Acid Receptor Splice Variants : Partin, Kathryn M. et al. ; Molecular Pharmacology, No. 46, 1994 pp. 129–138.

*Primary Examiner*—Peter O'Sullivan
*Attorney, Agent, or Firm*—Armstrong, Westerman, Hattori, McLeland & Naughton

[57] ABSTRACT

A method comprising administering a sulfonamide derivative to a patient requiring activation of glutamate receptors, the sulfonamide derivative represented by the formula

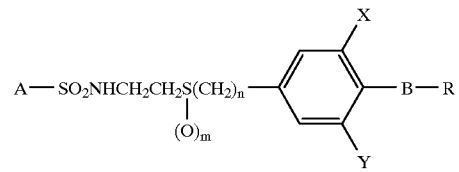

wherein A is a napthyl group, a pyridyl group, a phenyl group, a phenyl group substituted by 1 to 5 members selected from the group consisting of a halogen atom, an alkyl group having 1 to 40 carbon atoms, an alkoxy group having 1 to 4 carbon atoms, a nitro group, and an acetamido group, or an alkyl group having 1 to 20 carbon atoms; B is an alkylene group having 1 to 3 carbon atoms, a group of —OCH$_2$— or a group of —CH=CH—; X and Y are the same or different, and are each a hydrogen atom or a fluorine atom; R is a carboxy group, an alkoxycarbonyl group having 2 to 5 carbon atoms, a hydroxymethyl group or a group of

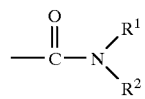

wherein $R_1$ is a hydrogen atom or an alkyl group having 1 to 3 carbon atoms; and $R_2$ is a hydrogen atom, a hydroxyl group, an alkyl group having 1 to 3 carbon atoms, a carboxymethyl group or an alkoxycarbonylmethyl group having 3 to 6 carbon atoms; m is an integer from 0 to 2; and n is an integer from 0 to 3, or an pharmaceutically acceptable salt thereof, as an effective ingredient. The agonist is efficacious in the medical treatment of nerve degenerative disorders.

3 Claims, No Drawings

GLUTAMIC ACID RECEPTOR AGONIST

This application is a 371 of PCT/JP96/00379, filed Feb. 20, 1996.

SUMMARY OF THE INVENTION

The present invention relates to an agonist (including a potentiator) for glutamate receptors. In detail the present invention relates to an agonist for glutamate receptors comprising a sulfonamide derivative or a pharmaceutically acceptable salt thereof as a effective ingredient.

BACKGROUND OF THE INVENTION

Amino acids which cause excitatory pastsynaptic potential are called as excitatory amino acids (EAA) and such acidic amino acids as L-glutamate, L-aspartate, L-homocysteine acid and quinolinic acid are known as internal substances. It is presumed that neurons using the said amino acids as the transmitters play the central role in the excitatory neurons of the mammalian brain. As a result of the recent rapid progress of the active researches conducted on the mechanism of the EAA transmission the relationship between a wide range of functions of the brain and the disorders of the brain is being unraveled. It has been found that in medicaments causing the disorders very similar to schizophrenia is there is a medical substance which intercepts the actions of the EAA receptors of the type of NMDA(N-methyl-D-aspartate). Accordingly strong attentions have been drawn on a probable participation of the disorders of the EAA transmission in schizophrenia.

As mentioned above the L-glutamate or the L-aspartate, which are amino acids, is a neurotransmitter causing the primary excitotoxic action in the central nervous system. By a number of researches it has been unraveled that the above-mentioned excitatory amino acid relates to a wide range of neurophysiological functions including synaptic transmission, the regulation and the long-term potentiation of neurotransmitters, learning and memory, the flexibility of synaptic generation, ischemic hypoxic disorders and neuronal death, and the cause of several neurodegenerative disorders.

For example, in Alzheimer's or cerebrovascular dementia distinguishing primarily the deterioration of the brain actions the deterioration of glutamatergic transmission is considered to be the cause, and also, the disorder of the glutamatergic transmission is found in schizophrenia.

Glutamate receptors which exist locally in synaps have been classified into the followings according to the receptor's affinity with specific ligand and electrophysiological or neurochemistric actions.

The NMDA(N-methyl-D-aspartate) receptor related to an ion channel characterizing the penetrability of monovalent and divalent cations such as sodium ions and calcium ions and the blockade of magnesium ions.

The AMPA (α-amino-3-hydroxy-5-methyl-4-isoxazolepropionic acid) receptor related to an ion channel characterizing the penetrability of monovalent cations such as sodium.

The KA (kainate) receptor which is similar to the AMPA receptor in the ion characteristics but different from the AMPA receptor in both the conductance and the level of desensitization.

(The AMPA receptor and the KA receptor are sometime called collectively as the non-NMDA receptor.)

It is useful to develop potentiating substances of glutamatergic transmission to be used for the prophylactic and medical treatment of the neurodegenerative disorders in the said state of diseases.

DISCLOSURE OF THE INVENTION

The object of the present invention is to provide an excellent agonist for glutamate receptors potentiating the actions of glutamate receptors comprising a sulfonamide derivative.

The inventors have studied with utmost effort to develop medical substances potentiating glutamatergic transmission to be used for the prophylactic and medical treatment of the neurodegenerative disorders in the state of diseases and succeeded in finding the potentiation of the response of glutamate receptors by sulfonamide derivatives. And the present invention has been accomplished on the basis of these results.

The invention is an agonist for glutamate receptors comprising a sulfonamide derivative represented by the following formula I

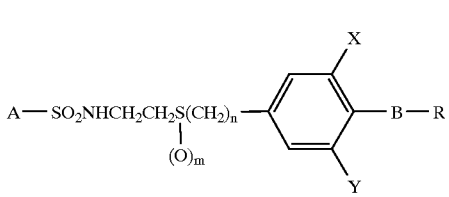

[wherein A is a naphthyl group, a pyridyl group, a phenyl group, a phenyl group substituted by 1 to 5 members selected from the group consisting of a halogen atom, an alkyl group having 1 to 4 carbon atoms, an alkoxy group having 1 to 4 carbon atoms, a nitro group and an acetamido group, or an alkyl group having 1 to 20 carbon atoms, B is an alkylene group having 1 to 3 carbon atoms, a group of —OCH$_2$— of a group of —CH=CH—, X and Y are the same or different, and are each a hydrogen atom or a fluorine atom, R is a carboxy group, an alkoxycarbonyl group having 2 to 5 carbon atoms, a hydroxymethyl group or a group of

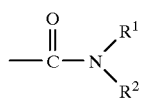

(wherein R$^1$ is a hydrogen atom or an alkyl group having 1 to 3 carbon atoms, and R$^2$ is a hydrogen atom, a hydroxyl group, an alkyl group having 1 to 3 carbon atoms, a carboxymethyl group or an alkoxycarbonyl methyl group having 3 to 6 carbon atoms), m is an integer from 0 to 2, n is an integer from 0 to 3], or a pharmaceutically acceptable salt thereof as an effective ingredient.

The desirable mode of the present invention is a sulfonamide derivative represented by the following formula I'

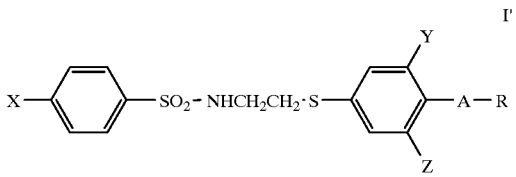

[wherein X and Y are the same or different, and are each a hydrogen atom or a halogen atom, A is a methylene group or a group of —OCH₂13 and R is a carboxy group or an alkoxycarbonyl group having 2 to 5 carbon atoms or a group of

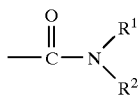

(wherein R¹ is a hydrogen atom or an alkyl group having 1 to 3 carbon atoms, and R² is a hydrogen atom, a hydroxyl group, an alkyl group having 1 to 3 carbon atoms, a carboxymethyl group or an alkoxycarbonylmethyl group having 3 to 6 carbon atoms), m is an integer from 0 to 2, n is an integer from 0 to 3], or a pharmaceutically acceptable salt thereof as an effective ingredient.

In the present invention, the alkyl group refers to a straight or branched chain alkyl group such as, a methyl group, an ethyl group, a propyl group, an isopropyl group, a butyl group, an isobutyl group, a pentyl group, an isopentyl group, a hexyl group, an octyl group, a decyl group, a hexadecyl group and an eicosyl group. The alkoxy group refers to a straight or branched chain alkoxy group such as, a methoxy group, an ethoxy group, a propoxy group, an isopropoxy group, a butoxy group and an isobutoxy group. The halogen atom refers to a fluorine atom, a chlorine atom, a bromine atom and iodine atom. The alkylene group refers to a straight or branched chain alkylene group such as, a methylene group, an ethylene group, a propylene group and a trimethylene group. The alkoxycarbonyl group refers to an alkoxycarbonyl group of which alkoxy moiety is straight or branched, for example, a methoxycarbonyl group, an ethoxycarbonyl group, a propoxycarbonyl group, an isopropoxycarbonyl group, a butoxycarbonyl group, an isobutoxycarbonyl group. The alkoxycarbonylmethyl group refers to those having a straight or branched chain alkoxy group, for example, a methoxycarbonylmethyl group, an ethoxycarbonylmethyl group, a propoxycarbonylmethyl group and an isopropoxycarbonylmethyl group. The salt of the compound of the present invention refers to a pharmaceutically acceptable salt, for example, sodium salt, potassium salt, calcium salt, ammonium salt and aluminium salt.

Among preferred compounds of the present invention are compounds of Formula I wherein A is a phenyl group substituted by 1 to 4 members selected from the group consisting of a halogen atom, an alkyl group having 1 to 4 carbon atoms, an alkoxy group having 1 to 4 carbon atoms, a nitro group and an acetamido group, B is an alkylene group having 1 to 3 carbon atoms or a group of —OCH₂—, X and Y are the same or different, and are each a hydrogen atom or a fluorine atom, R is a carboxy group or an alkoxycarbonyl group having 2 to 5 carbon atoms, m is an integer of 0 to 2 and n is 0. Among further preferred compounds are 2,6-difluoro-4-[2-(4-chlorophenylsulfonylamino)ethylthio]phenoxyacetic acid, 2,6-difluoro-4-[2-(4-methylphenylsulfonylamino)ethylthio]phenoxyacetic acid, 4-[2-(4-fluorophenylsulfonylamino)ethylthio]phenylacetic acid, 4-[2-(4-bromophenylsulfonylamino)ethylthio]phenylacetic acid, 4-[2-(4-methoxyphenylsulfonylamino)ethylthio]phenylacetic acid, 4-[2-(4-nitrophenylsulfonylamino)ethylthio]phenylacetic acid, 2,6-difluoro-4-[2-(4-fluorophenylsulfonylamino)ethylthio]phenoxyacetic acid, 2,6-difluoro-4-[2-(4-bromophenylsulfonylamino)ethylthio]phenoxyacetic acid, 2,6-difluoro-4-[2-(4-nitrophenylsulfonylamino)ethylthio]phenoxyacetic acid and 2,6-difluoro-4-[2-(4-methoxyphenylsulfonylamino)ethylthio]phenoxyacetic acid.

The compound of Formula I of the present invention can be prepared according to the following methods.

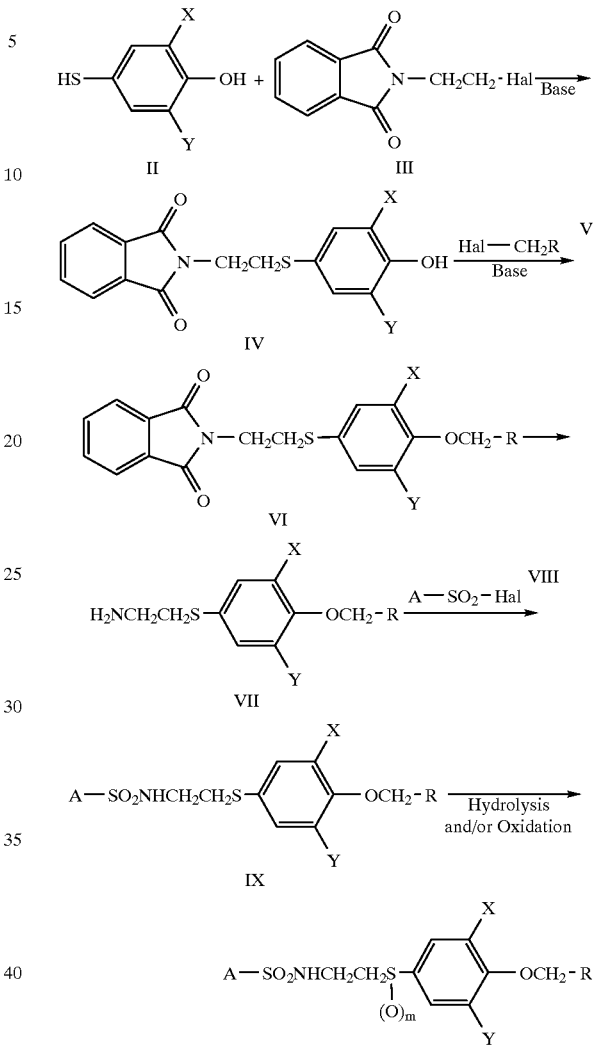

(1) The compound of Formula I wherein n is O, B is —OCH₂— can be prepared according to a following reaction scheme (wherein X,Y and R are as defined above, and Hal is a halogen atom).

A compound of Formula II (known or prepared by a known manner) is reacted with a compound of Formula III in a solvent in the presence of a base to give a compound of Formula IV. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N, N-dimethylformamide, dimethyl sulfoxide, acetone, ethanol, isopropanol, methanol, tetrahydrofuran, acetonitrile and water.

Then, a compound of Formula IV is reacted with a compound of Formula V in the presence of a base to give a compound of Formula VI. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a reaction accelerator such as phase-transfer catalysts (e.g. trimethylbenzylammonium chloride) and sodium iodide, and a solvent, for example, reaction-inert solvents such as methylene chloride, chloroform, N,N-dimethylformamide, dimethyl sulfoxide, acetone, ethanol, isopropanol, methanol, tetrahydrofuran, acetonitrile and water.

The phthalimino group of the compound of Formula VI is eliminated by an ordinary manner, for example, by treating with hydrazine, N-methylhydrazine or N,N-dimethylhydrazine in the absence or presence of a solvent to give a compound of Formula VII. Examples of the solvent are reaction-inert solvents such as methanol, ethanol, dichloromethane, tetrahydrofuran and chloroform. The compound of Formula VII can be isolated in the form of a salt, e.g. the hydrochloride, or can be used in the solution for the next reaction without any isolations.

The compound of Formula VII is reacted with a compound of Formula VIII in the presence of a base to give a compound of Formula IX. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a solvent, for example, reaction-inert solvents such as dichloromethane, chloroform, tetrahydrofuran and acetonitrile.

A compound of Formula IX can also be converted, by hydrolysis of ester or oxidation of the sulfur atom, into a different compound of the present invention. The hydrolysis of ester can be carried out according to an ordinary manner under the alkali condition (e.g. by using sodium hydroxide and potassium hydroxide) and the oxidation of the sulfur atom can be carried out according to an usual manner (e.g. by using hydrogen peroxide or m-chloroperbenzoic acid).

The compound of Formula II wherein X=Y=a fluorine atom, or X=a hydrogen atom and Y=a fluorine atom, can be synthesized by being subjected to sulfonation of 2,6-difluorophenol or 2-fluorophenol by a known sulfonation method (e.g. by using chlorosulfonic acid), halogenation in order to introduce a halosulfonyl group, and reduction by an ordinary reduction (e.g. by using tin or zinc under acidic conditions).

(2) The compound of Formula I wherein n=O and B is —OCH$_2$— can also be prepared according to the following reaction scheme (wherein X, Y and R are as defined above, and Hal is a halogen atom).

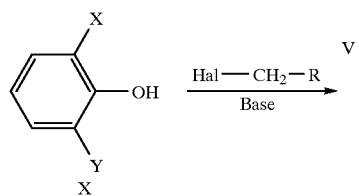

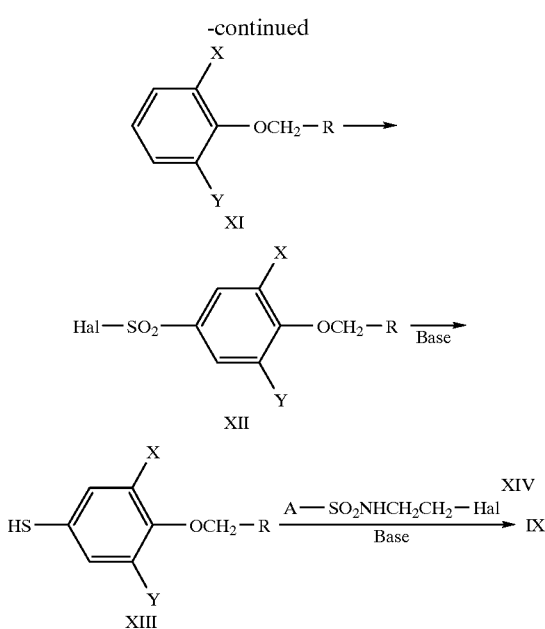

A compound of Formula X is reacted with a compound of Formula V in the presence of a base to give a compound of Formula XI. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). In this reaction, there can be used a reaction accelerator such as phase-transfer catalysts (e.g. trimethylbenzylammonium chloride) and sodium iodide, and a reaction-inert solvent such as methylene chloride, chloroform, N, N-dimethylformaide, dimethyl sulfoxide, acetone, ethanol, isopropanol, methanol, tetrahydrofuran, acetonitrile and water.

Then, the compound of Formula XI is subjected to sulfonation (e.g. by an ordinary manner using a sulfonating agent in a solvent) and halogenation to give a compound of Formula XII. Examples of the sulfonating agent are sulfuric acid, fuming sulfuric acid, sulfuric anhydride and chlorosulfonic acid. For halogenation, a halogenating agent (e.g. oxalyl chloride, thionyl chloride, phosphorus trichloride, phosphorus pentachloride, phosphoryl chloride and chlorosulfonic acid) is used. Further, a reaction accelerator (e.g. sodium chloride) can be used. Examples of the solvent are reaction-inert solvents such as carbon tetrachloride, methylene chloride, chloroform and 1,1,2,2-tetrachloroethane.

The compound of Formula XII is reduced by an ordinary manner (e.g. using tin, zinc or stannous chloride under acidic conditions) to give a compound of Formula XIII.

The compound of Formula XIII is reacted with the compound of Formula IV in the presence of a base in a solvent to give a compound of Formula IX. Examples of the base are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N,N-dimethylformamide, dimethyl sulfoxide, acetone, ethanol, isopropanol, methanol, tetrahydrofuran, acetonitrile and water.

(3) The compound of Formula I wherein n=O and B is an alkylene group or a group of —CH=CH— can be prepared by a reaction similar to that of the item (1) using a compound represented by the following formula:

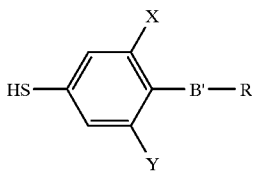

(wherein X, Y and R are as defined above, B' is B other than a group of —OCH$_2$—) in place of the compound of Formula II in the reaction scheme.

(4) In order to prepare the compound of Formula I wherein n is 1, 2 or 3, a compound of the formula:

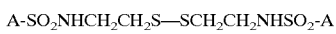

(wherein A is as defined above) is converted into a compound of the formula

(wherein A is as defined above) by an ordinary convertion of a disulfide into a mercaptane (e.g. by reduction using tributylphosphine), and the resulting compound, after isolation or without isolation, is reacted with a compound of the formula

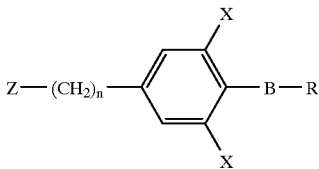

(wherein X, Y, B, R and n are as defined above, and Z is a methylsulfonyloxy group, a chlorine atom, a bromine atom or an iodine atom) in the presence of a base, and further is subjected to hydrolysis of ester as necessary to give the compound of Formula I of the present invention.

Examples of the base used herein are inorganic bases (e.g. potassium carbonate, sodium carbonate, calcium carbonate, sodium hydroxide, potassium hydroxide, calcium hydroxide, sodium hydride and sodium amide), alcoholates (e.g. sodium methylate and potassium t-butoxide), and organic amines (e.g. triethylamine and diisopropylethylamine). Examples of the solvent are reaction-inert solvents such as N, N-dimethylformamide, dimethylsulfoxide, acetone, ethanol, isopropanol, methanol, tetrahydorofuran, acetonitrile and water.

For embodiment of the present invention the compound of the invention can be employed as a range of form of the conventional pharmaceutical compositions, namely, powder, granule, tablet, glycocalyx, ampoule, capsule and utilized as doses for oral, hypodermic, intramuscular, intravenous and suppository administrations.

In production of the above-mentioned form of pharmaceutical compositions, of course, such additives as extending, bonding, disintegrating agents, pH regulators and resolvents can be placed into them.

The unit dosage of the compound of the present invention to the subject in need of treatment many varies depending upon the age, the kind and the state of disease and an amount of 1 to 5000 mg of the compound daily may be divided into 1 to several doses and administrated.

[BEST EMBODIMENTS OF THE INVENTION]

The present invention is illustrated in more detail by the following examples.

EXAMPLE 1

Chlorosulfonic acid (112.6 g) was added dropwise with ice cooling to 2,6-difluorophenol (25 g). The reaction mixture was stirred at room temperature for an hour and poured into ice-water (600 ml), and the separated oily substance was extracted with methylene chloride. The methylene chloride layer was washed successively with water and a saturated aqueous sodium chloride solution, and dried over anhydrous magnesium sulfate. The solvent was evaporated under reduced pressure to give 4-chlorosulfonyl-2,6-difluorophenol (31.5 g).

$^1$H-NMR (CDCl$_3$)δ:
6.29(1H, s), 7.50–7.80(2H, m)

To a mixture of 4-chlorosulfonyl-2,6-difluorophenol (31.5 g), tin (87.8 g) and methanol (320 ml) was added dropwise concentrated hydrochloric acid (80 ml) while the reaction temperature was kept at 40° C. The reaction mixture was heated at reflux for 3 hours and poured into ice water (600 ml), and the separated oily substance was extracted with methylene chloride. The methylene chloride layer was washed with a saturated aqueous sodium chloride solution and dried over anhydrous magnesium sulfate. The solvent was evaporated under reduced pressure to give the residue, to which were then added potassium carbonate (24.2 g) and N,N-dimethylformamide (200 ml) under an argon atmosphere. A solution of N-(2-bromoethyl) phthalimide (30.1 g) in N,N-dimethylformamide (100 ml) was added dropwise under ice cooling, and the reaction mixture was stirred at room temperature for 16 hours and poured into 7% hydrochloric acid (1200 ml). The separated oily substance was extracted with ethyl acetate. The ethyl acetate layer was washed with a saturated aqueous sodium chloride solution and dried over anhydrous magnesium sulfate. The solvent was evaporated under reduced pressure to give a residue, which was then crystallized from ethyl acetate—n-hexane to give 4-[2-(phthalimid-2-yl)ethylthio]-2,6-difluorophenol (27.5 g).

m.p. 143–144.5° C.

To a mixture of 4-[2-(phthalimid-2-yl)ethylthio]-2,6-difluorophenol (15 g), potassium carbonate (9.1 g) and N,N-dimethylformamide (50 ml) was added dropwise under ice cooling ethyl bromoacetate (7.4 g). The reaction mixture was stirred at room temperature for 16 hours, and poured into a mixture of concentrated hydrochloric acid (50 ml) and ice (450 g). The separated oily substance was extracted with ethyl acetate, and the ethyl acetate layer was washed with a saturated aqueous sodium chloride solution and dried over anhydrous magnesium sulfate. The solvent was evaporated under reduced pressure to give a residue, which was then crystallized from acetone—n-hexane to give ethyl 4-[2-(phthalimid-2-yl)ethylthio]-2,6-difluorophenoxyacetate (17 g).

m.p. 90.5–92° C.

To a mixture of ethyl 4-[2-(phthalimid-2-yl)ethylthio]-2,6-difluorophenoxyacetate (6 g), ethanol (50 ml) and methylene chloride (50 ml) was added hydrazine monohydrate (1.4 g), and the reaction mixture was stirred at room temperature for 16 hours. After removal of the resulting insolubles by filtration, the filtrate was washed with water and dried over anhydrous magnesium sulfate and filtered to remove the insolubles. To the filtrate was added triethylamine (1 g), and then 4-chlorophenylsulfonyl chloride (1.8 g) was added dropwise under ice cooling. The reaction mixture was stirred at room temperature for an hour, washed successively with water, an aqueous sodium bicarbonate solution and a saturated aqueous sodium chloride solution and dried over anhydrous magnesium sulfate. After evaporation of the solvent under reduced pressure, the resulting residue was chromatographed on silica gel column (eluent; methylene chloride:n-hexane=2:1) to give ethyl 4-[2-(phenylsulfonylamino)ethylthio]-2,6-difluorophenoxyacetate (Compound No. 1) (1.5 g).

$^1$H-NMR (CDCl$_3$)δ:
1.28(3H, t, J=6 Hz), 2.97(2H, m), 3.14(2H, m), 4.25(2H, q, J=6 Hz), 4.72(2H, s), 4.88(1H, t, J=6 Hz), 6.80(2H, m), 7.46–7.65(3H, m), 7.84(2H, m)

Following the similar manner, there were obtained the following compounds.

Ethyl 4-[2-(4-chlorophenylsulfonylamino)ethylthio]-2,6-difluorophenoxyacetate (Compound No. 2)

$^1$H-NMR (CDCl$_3$)δ:
1.29(3H, t, J=6 Hz), 2.98(2H, m), 3.14(2H, m), 4.25(2H, q, J=6 Hz), 4.73(2H, s), 4.95(1H, t, J=6 Hz), 6.83(2H, m), 7.49(2H, m), 7.78(2H, m)

Ethyl 4-[2-(4-methylphenylsulfonylamino)ethylthio]-2,6-difluorophenoxyacetate (Compound No. 3)

$^1$H-NMR (CDCl$_3$)δ:
1.29(3H, t, J=6 Hz), 2.43(3H, s), 2.95(2H, m), 3.12(2H, m), 4.25(2H, q, J=6 Hz), 4.72(2H, s), 4.82(1H, t, J=6 Hz), 6.79(2H, m), 7.30(2H, m), 7.72(2H, m)

Methyl 2,6-difluoro-4-[2-(4-fluorophenylsulfonylamino)ethylthio]phenoxyacetate (Compound No. 4)

$^1$H-NMR (CDCl$_3$)δ:
3.0–3.3(4H, m), 3.71(3H, s), 4.84(2H, s), 7.08(2H, m), 7.9–8.1(2H, m), 8.3–8.4(2H, m)

Methyl 2,6-difluoro-4-[2-(4-bromophenylsulfonylamino)ethylthio]phenoxyacetate (Compound No. 5)

$^1$H-NMR (CDCl$_3$)δ:
2.8–3.0(4H, m), 3.76(3H, s), 4.75(2H, s), 5.10(1H, brs), 7.05(2H, m), 7.6–8.1(4H, m)

Methyl 2,6-difluoro-4-[2-(4-nitrophenylsulfonylamino)ethylthio]phenoxyacetate (Compound No. 6)

$^1$H-NMR (CDCl$_3$)δ:
2.8–3.0(4H, m), 3.75(3H, s), 4.76(2H, s), 5.10(1H, brs), 7.08(2H, m), 8.02(2H, d, J=8.8 Hz), 8.40(2H, d, J=8.8 Hz)

Methyl 2,6-difluoro-4-[2-(methylsulfonylamino)ethylthio]phenoxyacetate (Compound No. 7)

$^1$H-NMR (CDCl$_3$)δ:
2.93(3H, s), 2.9–3.3(4H, m), 3.75(3H, s), 4.70(2H, s), 5.10(1H, brs), 6.91(2H, m)

Methyl 2,6-difluoro-4-[2-(octylsulfonylamino)ethylthio]phenoxyacetate (Compound No. 8)

$^1$H-NMR (CDCl$_3$)δ:
0.7–0.9(3H, m), 1.1–1.4(12H, m), 1.6–1.8(2H, m), 2.8–3.3(4H, m), 3.72(3H, s), 4.67(2H, s), 4.82(1H, t, J=5.9 Hz), 6.86(2H, m)

Methyl 2,6-difluoro-4-[2-(4-hexadecylsulfonylamino)ethylthio]phenoxyacetate (Compound No. 9)

$^1$H-NMR (CDCl$_3$)δ:
0.8–1.0(3H, m), 1.1–1.4(28H, m), 1.7–1.9(2H, m), 2.9–3.3(4H, m), 3.78(3H, s), 4.73(2H, s), 5.14(1H, t, J=6 Hz), 6.94(2H, m)

Methyl 2,6-difluoro-4-[2-(4-methoxyphenylsulfonylamino)ethylthio]phenoxyacetate (Compound No. 10)

$^1$H-NMR (CDCl$_3$)δ:
2.8–3.0(4H, m), 3.69(3H, s), 3.77(3H, s), 4.63(2H, s), 5.07(1H, t, J=6.1 Hz), 6.70(2H, m), 6.86(2H, d, J=8.9 Hz), 7.67(2H, d, J=8.9 Hz)

EXAMPLE 2

Following a procedure similar to that of Example 1 using 2-fluorophenol as a material, there were obtained the following compounds.

Ethyl 4-[2-(phenylsulfonylamino)ethylthio]-2-fluorophenoxyacetate (Compound No. 11)

$^1$H-NMR (CDCl$_3$)δ:
1.30(3H, t, J=7 Hz), 2.90(2H, t, J=6 Hz), 3.09(2H, m), 4.27(2H, q, J=7 Hz), 4.67(2H, s), 5.11(1H, t, J=7 Hz), 6.80(1H, t, J=8 Hz), 7.00(2H, m), 7.51(3H, m), 7.82(2H, m)

Ethyl 4-[2-(4-chlorophenylsulfonylamino)ethylthio]-2-fluorophenoxyacetate (Compound No. 12)

$^1$H-NMR (CDCl$_3$)δ:
1.30(3H, t, J=6 Hz), 2.91(2H, m), 3.08(2H, m), 4.27(2H, q, J=6 Hz), 4.68(2H, s), 4.90(11H, t, J=6 Hz), 6.80(1H, t, J=8 Hz), 6.99(3H, m), 7.49(2H, m), 7.75(2H, m)

Ethyl 4-[2-(4-methylphenylsulfonylamino)ethylthio]-2-fluorophenoxyacetate (Compound No. 13)

$^1$H-NMR (CDCl$_3$)δ:
1.30(3H, t, J=6 Hz), 2.42(3H, s), 2.89(2H, m), 3.07(2H, m), 4.27(2H, q, J=6 Hz), 4.67(2H, s), 4.72(1H, m), 6.80(1H, t, J=8 Hz), 6.95(3H, m), 7.28(2H, m), 7.68(2H, m)

Methyl 2-fluoro-4-[2-(4-fluorophenylsulfonylamino)ethylthio]phenoxyacetate (Compound No. 14)

$^1$H-NMR (CDCl$_3$)δ:
2.8–3.2(4H, m), 3.78(3H, s), 4.78(2H, s), 5.2(1H, brs), 7.0–8.1(7H, m)

Methyl 2-fluoro-4-[2-(4-bromophenylsulfonylamino)ethylthio]phenoxyacetate (Compound No. 15)

$^1$H-NMR (CDCl$_3$)δ:
2.8–3.2(4H, m), 3.78(3H, s), 4.78(2H, s), 5.2(1H, brs), 7.0–8.0(7H, m)

Methyl 2-fluoro-4-[2-(4-methoxyphenylsulfonylamino)ethylthio]phenoxyacetate (Compound No. 16)

$^1$H-NMR (CDCl$_3$)δ:
2.8–3.2(4H, m), 3.78(3H, s), 3.84(3H, s), 4.78(2H, s), 5.2(1H, brs), 7.0–7.3(3H, m), 7.5–7.8(4H, m)

Methyl 2-fluoro-4-[2-(4-nitrophenylsulfonylamino)ethylthio]phenoxyacetate (Compound No. 17)

$^1$H-NMR (CDCl$_3$)δ:
2.8–3.1(4H, m), 3.78(3H, s), 4.77(2H, s), 5.2(1H, brs), 7.0–7.3(3H, m), 8.0–8.6(4H, m)

Methyl 2-fluoro-4-[2-(methylsulfonylamino)ethylthio]phenoxyacetate (Compound No. 18)

$^1$H-NMR (CDCl$_3$)δ:
2.95(3H, s), 2.8–3.2(4H, m), 3.77(3H, s), 4.75(2H, s), 5.1(1H, brs), 6.9–7.4(3H, m)

Methyl 2-fluoro-4-[2-(octylsulfonylamino)ethylthio]phenoxyacetate (Compound No. 19)

$^1$H-NMR (CDCl$_3$)δ:
0.8–1.0(3H, m), 1.2–1.8(14H, m), 2.8–3.2(4H, m), 3.78(3H, s), 4.77(2H, s), 5.1(1H, brs), 7.0–7.4(3H, m)

Methyl 2-fluoro-4-[2-(hexadecylsulfonylamino)ethylthio]phenoxyacetate (Compound No. 20)

$^1$H-NMR (CDCl$_3$)δ:
0.8–1.0(3H, m), 1.2–1.8(30H, m), 2.8–3.2(4H, m), 3.77(3H, s), 4.75(2H, s), 5,1(1H, brs), 6.9–7.4(3H, m)

EXAMPLE 3

To a mixture of 4-mercaptophenol (3.78 g), potassium carbonate (8.2 g) and N,N-dimethylformamide (40 ml) was added dropwise under ice cooling a solution of N-(2-bromoethyl)phthalimide (7.62 g) in N,N-dimethylformamide (50 ml). The reaction mixture was stirred at room temperature for 16 hours and poured into 3% hydrochloric acid (220 ml), and the resulting crystals were collected by filtration and dried to give N-[2-(4-hydroxyphenylthio)ethyl]phthalimide (9.1 g).

m.p. 124–125° C.

To a mixture of N-[2-(4-hydroxyphenylthio)ethyl]-phthalimide (7.8 g) obtained above, potassium carbonate (7.2 g) and N,N-dimethylformamide (50 ml) was added dropwise under ice cooling ethyl bromoacetate (2.9 ml). The reaction mixture was warmed to 60° C., stirred for 3 hours, poured into 3% hydrochloric acid (220 ml) and extracted with ethyl acetate. The ethyl acetate layer was washed twice with a saturated aqueous sodium chloride solution and dried over anhydrous magnesium sulfate. Evaporation of the solvent under reduced pressure gave a residue, which was then recrystallized from n-hexane to give ethyl 4-[2-(phthalimid-2-yl)ethylthio]phenoxyacetate (10.0 g).

m.p. 91–92° C.

A mixture of ethyl 4-[2-(phthalimid-2-yl)ethylthio] phenoxyacetate (9.9 g), methylene chloride (100 ml), ethanol (100 ml) and hydrazine monohydrate (2.5 ml) was stirred at room temperature for 16 hours. After removal of the resulting insolubles by filtration, the filtrate was washed with water and dried over anhydrous magnesium sulfate, and the insolubles were removed by filtration.

To the filtrate obtained above was added triethylamine (3.8 ml) and then benzenesulfonyl chloride (4.54 g) was added dropwise under ice cooling. The reaction mixture was stirred at room temperature for 30 minutes, washed successively with water, an aqueous sodium bicarbonate solution and a saturated aqueous sodium chloride solution and dried over anhydrous magnesium sulfate. Evaporation of the solvent under reduced pressure gave a residue, which was then chromatographed on silica gel column (eluent; ethyl acetate:n-hexane=2:3) to give ethyl 4-[2-(phenylsulfonylamino)ethylthio]phenoxyacetate (Compound No. 21) (5.9 g).

$^1$H-NMR (CDCl$_3$)δ:
1.29(3H, t, J=7 Hz), 2.83(2H, t, J=6 Hz), 3.04(2H, brq), 4.27(2H, q, J=7 Hz), 4.60(2H, s), 5.10(1H, brs), 6.76 (2H, m), 7.20(2H, m), 7.51(3H, m), 7.80(2H, m)

Following a similar manner to that of Example 3, there were obtained the following compounds.

Ethyl 4-[2-(4-chlorophenylsulfonylamino)ethylthio] phenoxyacetate (Compound No. 22)
$^1$H-NMR (CDCl$_3$)δ:
1.30(3H, t, J=7 Hz), 2.86(2H, t, J=6 Hz), 3.04(2H, q, J=6 Hz), 4.28(2H, q, J=7 Hz), 4.60(2H, s), 4.90(1H, brt), 6.78(2H, m), 7.18(2H, m), 7.46(2H, m), 7.73(2H, m)

Methyl 4-[2-(4-methylphenylsulfonylamino)ethylthio] phenoxyacetate (Compound No. 23)
$^1$H-NMR (CDCl$_3$)δ:
2.37(3H, s), 2.8–3.2(4H, m), 3.76(3H, s), 4.66(2H, s), 5.2(1H, brs), 6.9–7.7(8H, m)

Methyl 4-[2-(4-methoxyphenylsulfonylamino)ethylthio] phenoxyacetate (Compound No. 24)
$^1$H-NMR (CDCl$_3$)δ:
2.8–3.2(4H, m), 3.76(3H, s), 3.83(3H, s), 4.65(2H, s), 5.2(1H, brs), 6.9–7.2(4H, m), 7.3–7.7(4H, m)

Methyl 4-[2-(4-fluorophenylsulfonylamino)ethylthio] phenoxyacetate (Compound No. 25)
$^1$H-NMR (CDCl$_3$)δ:
2.8–3.1(4H, m), 3.78(3H, s), 4.66(2H, s), 5.2(1H, brs), 6.9–7.3(4H, m), 7.5–8.0(4H, m)

Methyl 4-[2-(4-bromophenylsulfonylamino)ethylthio] phenoxyacetate (Compound No. 26)
$^1$H-NMR (CDCl$_3$)δ:
2.8–3.2(4H, m), 3.78(3H, s), 4.68(2H, s), 5.2(1H, brs), 6.9–7.4(4H, m), 7.7–8.1(4H, m)

Methyl 4-[2-(2,5-dichlorophenylsulfonylamino) ethylthio]phenoxyacetate (Compound No. 27)
$^1$H-NMR (CDCl$_3$)δ:
2.8–3.2(4H, m), 3.77(3H, s), 4.67(2H, s), 5.2(1H, brs), 6.9–7.3(4H, m), 7.8–8.0(3H, m)

Methyl 4-[2-(2,4,5-trichlorophenylsulfonylamino) ethylthio]phenoxyacetate (Compound No. 28)
$^1$H-NMR (CDCl$_3$)δ:
2.8–3.2(4H, m), 3.76(3H, s), 4.66(2H, s), 6.9–7.2(4H, m), 5.1(1H, brs), 8.0–8.1(2H, m)

Methyl 4-[2-(2,3,4,5,6-pentafluorophenylsulfonylamino) ethylthio]phenoxyacetate (Compound No. 29)
$^1$H-NMR (CDCl$_3$)δ:
2.9–3.3(4H, m), 3.78(3H, s), 4.67(2H, s), 5.1(1H, brs), 6.9–7.3(4H, m)

Methyl 4-[2-(2,4,6-trimethylphenylsulfonylamino) ethylthio]phenoxyacetate (Compound No. 30)
$^1$H-NMR (CDCl$_3$)δ:
2.26(3H, s), 2.49(6H, s), 2.8–3.2(4H, m), 3.78(3H, s), 4.66(2H, s), 5.2(1H, brs), 6.9–7.2(6H, m)

Methyl 4-[2-(2,4,6-triisopropylphenylsulfonylamino) ethylthio]phenoxyacetate (Compound No. 31)
$^1$H-NMR (CDCl$_3$)δ:
1.2–1.3(18H, m), 2.8–3.2(7H, m), 3.77(3H, s), 4.65(2H, s), 5.2(1H, brs), 6.8–7.2(6H, m)

Methyl 4-[2-(2-naphthylsulfonylamino)ethylthio] phenoxyacetate (Compound No. 32)
$^1$H-NMR (CDCl$_3$)δ:
2.8–3.2(4H, m), 3.78(3H, s), 4.65(2H, s), 5.2(1H, brs), 6.8–7.1(4H, m), 7.7–8.4(7H, m)

Methyl 4-[2-(4-nitrophenylsulfonylamino)ethylthio] phenoxyacetate (Compound No. 33)
$^1$H-NMR (CDCl$_3$)δ:
2.8–3.2(4H, m), 3.78(3H, s), 4.66(2H, s), 5.1(1H, brs), 6.9–7.2(4H, m), 8.0–8.4(4H, m)

Methyl 4-[2-(4-chloro-3-nitrophenylsulfonylamino) ethylthio]phenoxyacetate (Compound No. 34)
$^1$H-NMR (CDCl$_3$)δ:
2.8–3.2(4H, m), 3.76(3H, s), 4.66(2H, s), 5.2(1H, brs), 6.9–7.2(4H, m), 8.0–8.4(4H, m)

Methyl 4-[2-(4-acetylaminophenylsulfonylamino) ethylthio]phenoxyacetate (Compound No. 35)
$^1$H-NMR (CDCl$_3$)δ:
2.08(3H, s), 2.5–2.9(4H, m), 3.52(3H, s), 4.11(2H, s), 5.2(1H, brs), 6.7–7.5(8H, m)

Methyl 4-[2-(3-pyridylsulfonylamino)ethylthio] phenoxyacetate (Compound No. 36)
$^1$H-NMR (CDCl$_3$)δ:
2.8–3.2(4H, m), 3.77(3H, s), 4.68(2H, s), 5.1(1H, brs), 6.9–7.3(4H, m), 7.5–8.9(4H, m)

Methyl 4-[2-(3,5-dichloro-2-hydroxyphenylsulfonylamino)ethylthio]phenoxyacetate (Compound No. 37)
$^1$H-NMR (CDCl$_3$)δ:
2.8–3.1(4H, m), 3.76(3H, s), 4.65(2H, s), 5.2(1H, brs), 6.8–7.2(4H, m), 7.6–7.8(2H, m)

EXAMPLE 4

To a solution of ethyl 4-[2-(phenylsulfonylamino) ethylthio]phenoxyacetate (2 g) obtained in Example 3 in methylene chloride (30 ml) was added dropwise under ice cooling a solution of m-chloroperbenzoic acid (0.87 g) in methylene chloride (20 ml). The reaction mixture was stirred at room temperature for an hour, washed with an aqueous sodium bicarbonate solution and dried over anhydrous magnesium sulfate. Evaporation of the solvent under reduced pressure gave a residue, which was then chromatographed on silica gel column (eluent; ethyl acetate) and recrystallized from ethyl acetate to give ethyl 4-[2-(phenylsulfonylamino) ethylsulfinyl]phenoxyacetate (Compound No. 38) (1.76 g).

m.p. 116–118.5° C.

Following a similar manner to that of Example 4, there was obtained ethyl 4-[2-(4-chlorophenylsulfonylamino) ethylsulfinyl]-2,6-difluorophenoxyacetate (Compound No. 39).

m.p. 137–138° C.

EXAMPLE 5

To a solution of ethyl 4-[2-(phenylsulfonylamino) ethylthio]phenoxyacetate (1.8 g) obtained in Example 3 in methylene chloride (30 ml) was added dropwise under ice cooling a solution of m-chloroperbenzoic acid (1.57 g) in methylene chloride (40 ml). The reaction mixture was stirred at room temperature for an hour, washed with an aqueous sodium bicarbonate solution and dried over anhydrous magnesium sulfate. Evaporation of the solvent under reduced pressure gave a residue, which was chromatographed on silica gel column (eluent; ethyl acetate) to give ethyl 4-[2-(phenylsulfonylamino)ethylsulfonyl]phenoxyacetate (Compound No. 40) (1.94 g).

m.p. 86.5–88° C.

Following a similar manner to that of Example 5, there was obtained ethyl 4-[2-(4-chlorophenylsulfonylamino) ethylsulfonyl]-2,6-difluorophenoxyacetate (Compound No. 41).

m.p. 166–167° C.

EXAMPLE 6

Chlorosulfonic acid (87 ml) was added dropwise to ethyl phenylacetate (48 g), and the mixture was stirred at 40° C. for 30 minutes. The reaction mixture was poured into ice water (1000 ml), and the separated oily substance was extracted with methylene chloride. The methylene chloride layer was washed successively with water and a saturated aqueous sodium chloride solution and dried over anhydrous magnesium sulfate. Evaporation of the solvent under reduced pressure gave ethyl 4-chlorosulfonylphenylacetate (42 g).

$^1$H-NMR (CDCl$_3$)δ:

1.25(3H, t, J=7 Hz), 3.11(2H, s), 4.20(2H, q, J=7 Hz), 7.55(2H, m), 8.00(2H, m)

To a mixture of ethyl 4-chlorosulfonylphenylacetate (42 g) obtained above, tin (96 g) and methanol (320 ml) was added dropwise at 40° C. conc. hydrochloric acid (80 ml). The reaction mixture was heated at reflux for 3 hours and poured into ice water (600 ml), and the separated oily substance was extracted with methylene chloride. The methylene chloride layer was washed successively with water and a saturated aqueous sodium chloride solution and dried over anhydrous magnesium sulfate, and the solvent was evaporated under reduced pressure. To the resulting residue were added under an argon atmosphere potassium carbonate (16.4 g) and N,N-dimethylformamide (100 ml). Then, a solution of N-(2-bromoethyl)phthalimide (20.3 g) in N,N-dimethylformamide (100 ml) was added dropwise under ice cooling. The reaction mixture was stirred at room temperature for 16 hours and poured into 7% hydrochloric acid (1200 ml), and the separated oily substance was extracted with ethyl acetate. The ethyl acetate layer was washed with a saturated aqueous sodium chloride solution and dried over anhydrous magnesium sulfate. Evaporation of the solvent under reduced pressure gave a residue, which was chromatographed on silica gel column (eluent; methylene chloride:n-hexane=1:1) and crystallized from methylene chloride—n-hexane to give methyl 4-[2-(phthalimid-2-yl) ethylthio]phenylacetate (9.1 g).

m.p. 90–92° C.

Following a similar manner to that of Example 1 using methyl 4-[2-(phthalimid-2-yl)ethylthio]phenylacetate, there was obtained methyl 4-[2-(phenylsulfonylamino)ethylthio] phenylacetate (Compound No. 42).

$^1$H-NMR (CDCl$_3$)δ:

2.95(2H, t, J=7 Hz), 3.12(2H, m), 3.57(2H, s), 3.70(3H, s), 4.95(1H, brm), 7.16(3H, m), 7.50(2H, m), 7.82(2H, m)

In a similar manner, there were obtained the following compounds.

Methyl 4-[2-(4-chlorophenylsulfonylamino)ethylthio] phenylacetate (Compound No. 43)

$^1$H-NMR (CDCl$_3$)δ:

2.98(2H, m), 3.11(2H, m), 3.60(2H, s), 3.70(3H, s), 7.18(4H, m), 7.44(2H, m), 7.74(2H, m)

Methyl 4- [2- (4-methylphenylsulfonylamino) ethylthio] phenylacetate (Compound No. 44)

$^1$H-NMR (CDCl$_3$)δ:

2.43(3H, s), 2.95(2H, m), 3.10(2H, m), 3.58(2H, s), 3.70(3H, s), 4.93(1H, t, J=6 Hz), 7.18(4H, m), 7.28(2H, m), 7.71(2H, m)

Methyl 4-[2-(4-fluorophenylsulfonylamino)ethylthio] phenylacetate (Compound No. 45)

$^1$H-NMR (CDCl$_3$)δ:

2.9–3.3(4H, m), 3.55(2H, s), 3.78(3H, s), 5.1(1H, brs), 7.1–8.1(8H, m)

Methyl 4-[2-(4-bromophenylsulfonylamino)ethylthio] phenylacetate (Compound No. 46)

$^1$H-NMR (CDCl$_3$)δ:

2.9–3.2(4H, m), 3.56(2H, s), 3.77(3H, s), 5.2(1H, brs), 7.1–8.1(8H, m)

Methyl 4-[2-(4-methoxyphenylsulfonylamino)ethylthio] phenylacetate (Compound No. 47)

$^1$H-NMR (CDCl$_3$)δ:

2.9–3.2(4H, m), 3.55(2H, s), 3.78(3H, s) 3.82(3H, s), 5.2(1H, brs), 7.1–7.4(4H, m), 7.6–8.0(4H, m)

Methyl 4-[2-(4-nitrophenylsulfonylamino)ethylthio] phenylacetate (Compound No. 48)

$^1$H-NMR (CDCl$_3$)δ:

2.9–3.4(4H, m), 3.56(2H, s), 3.75(3H, s), 7.0–7.3(4H, m), 5.2(1H, brs), 8.0–8.5(4H, m)

Methyl 4-[2-(methylsulfonylamino)ethylthio] phenylacetate (Compound No. 49)

$^1$H-NMR (CDCl$_3$)δ:

2.90(3H, s), 2.9–3.3(4H, m), 3.55(2H, s), 3.76(3H, s), 5.2(1H, brs), 7.1–7.4(4H, m)

Methyl 4-[2-(octylsulfonylamino)ethylthio]phenylacetate (Compound No. 50)

$^1$H-NMR (CDCl$_3$)δ:

0.7–0.9(3H, m), 1.2–1.8(14H, m), 2.9–3.4(4H, m), 3.55 (2H, s), 3.76(3H, s), 5.1(1H, brs), 7.1–7.4(4H, m)

Methyl 4-[2-(hexadecylsulfonylamino)ethylthio]phenylacetate (Compound No. 51)

$^1$H-NMR (CDCl$_3$)δ:

0.7–0.9(3H, m), 1.2–1.8(30H, m), 2.9–3.4(4H, m), 3.56(2H, s), 3.78(3H, s), 5.2(1H, brs), 7.1–7.4(4H, m)

EXAMPLE 7

To a mixture of 3-(4-mercaptophenyl)propionic acid (1.82 g), potassium carbonate (5.6 g) and N,N-dimethylformamide (12 ml) was added N-(2-bromoethyl)phthalimide (2.54 g), and the mixture was stirred at room temperature for 3.5 hours. The reaction mixture was poured into 2% hydrochloric acid (150 ml), and extracted with ethyl acetate. The ethyl acetate layer was washed twice with a saturated aqueous sodium chloride solution and dried over anhydrous magnesium sulfate. Evaporation of the solvent under reduced pressure gave 3-{4-[2-(phthalimid-2-yl)ethylthio]phenyl}propionic acid (3.58 g).

m.p. 105.5–107° C.

A mixture of 3-{4-[2-(phthalimid-2-yl)ethylthio]phenyl}propionic acid (3.4 g), hydrazine monohydrate (3.85 ml) and methanol (30 ml) was heated at reflux with stirring for an hour. After cooling the reaction mixture, the resulting insolubles were removed by filtration, and the filtrate was evaporated under reduced pressure. The residue was chromatographed (Diaion HP-20, eluent; water—methanol) to give 3-[4-(2-aminoethylthio)phenyl]propionic acid (1.75 g)

m.p. 90–110° C.

To a mixture of 3-[4-(2-aminoethylthio)phenyl]propionic acid (0.8 g), triethylamine (1.6 ml) and methylene chloride (50 ml) was added 4-chlorophenylsulfonyl chloride (0.79 g), and the mixture was stirred at room temperature for 16 hours. The reaction mixture was washed successively with 3% hydrochloric acid and a saturated aqueous sodium chloride solution, and dried over anhydrous magnesium sulfate. Evaporation of the solvent under reduced pressure gave a residue, which was then crystallized from ethyl acetate—n-hexane to give 3-{4-[2-(4-chlorophenylsulfonylamino)ethylthio]phenyl}propionic acid (Compound No. 52) (1.07 g)

m.p. 117–119° C.

Following a similar manner to that of Example 7, there were obtained the following compounds.

3-{4-[2-(4-Methylphenylsulfonylamino)ethylthio]phenyl}propionic acid (Compound No. 53)

m.p. 127.3–130.4° C.

3-{4-[2-(4-Fluorophenylsulfonylamino)ethylthio]phenyl}propionic acid (Compound No. 54)

m.p. 135–136.5° C.

3-{4-[2-(4-Bromophenylsulfonylamino)ethylthio]phenyl}propionic acid (Compound No. 55)

m.p. 129.7–133.5° C.

3-{4-[2-(2,3,4,5,6-Pentafluorophenylsulfonylamino)ethylthio]phenyl}propionic acid (Compound No. 56)

m.p. 131.5–133.6° C.

Potassium 3-{4-[2-(2,4,6-trimethylphenylsulfonylamino)ethylthio]phenyl}propionate (Compound No. 57)

$^1$H-NMR (DMSO-d$_6$)δ:

1.65(1H, s), 2.1–2.2(2H, m), 2.25(3H, s), 2.51(6H, s), 2.7–2.9(6H, m), 6.99(2H, s), 7.08(4H, s)

3-{4-[2-(3,4-Dichloro-6-hydroxyphenylsulfonylamino)ethylthio]phenyl}propionic acid (Compound No. 58)

m.p. 139–141.4° C.

3-{4-[2-(3-Nitro-4-chlorophenylsulfonylamino)ethylthio]phenyl}propionic acid (Compound No. 59)

m.p. 125.1–127.7° C.

3-{4-[2-(4-Acetamidophenylsulfonylamino)ethylthio]phenyl}propionic acid (Compound No. 60)

m.p. 146.5–148.9° C.

3-{4-[2-(3-Pyridylsulfonylamino)ethylthio]phenyl}propionic acid (Compound No. 61)

m.p. 146.7–149.8° C.

EXAMPLE 8

A mixture of bis[2-(phenylsulfonylamino)ethyl]disulfide (1 g), tributylphosphine (0.72 ml) and 90% methanol (30 ml) was stirred under an argon atmosphere at room temperature for 30 minutes, and the reaction mixture was evaporated under reduced pressure. To the residue were added under an argon atmosphere triethylamine (1.4 ml) and ethanol (10 ml). Then, ethyl 4-chloromethylphenoxyacetate (1.05 g) was added, and the mixture was stirred at room temperature for 16 hours. The reaction mixture was evaporated under reduced pressure, and the resulting residue was chromatographed on silica gel column (eluent: ethyl acetate—n-hexane=1:3) to give ethyl 4-[2-(phenylsulfonylamino)ethylthiomethyl]phenoxyacetate (Compound No. 62) (1.04 g).

$^1$H-NMR (CDCl$_3$)δ:

1.30(3H, t, J=7 Hz), 2.49(2H, t, J=6 Hz), 3.02(2H, brs), 3.51(2H, s), 4.25(2H, q, J=7 Hz), 4.59(2H, s), 4.98(1H, brs), 6.80(2H, m), 7.13(2H, m), 7.55(3H, m), 7.83(2H, m)

In a similar manner, there was obtained the following Compound.

Ethyl 4-[2-(4-chlorophenylsulfonylamino)ethylthiomethyl]phenoxyacetate (Compound No. 63)

m.p. 52.5–53.5° C.

EXAMPLE 9

To a solution of methyl 4-formylcinnamate (5.58 g) in methanol (100 ml) was added sodium borohydride (0.4 g), and the mixture was stirred at room temperature for an hour. The reaction mixture was poured into water and extracted with methylene chloride. The methylene chloride layer was washed with a saturated aqueous sodium chloride solution and dried over anhydrous magnesium sulfate. Evaporation of the solvent under reduced pressure gave methyl 4-(hydroxymethyl)cinnamate (5.27 g).

m.p. 86–87° C.

To a mixture of methyl 4-(hydroxymethyl)cinnamate (4.1 g), triethylamine (3.1 ml) and methylene chloride (50 ml) was added dropwise under ice cooling methanesulfonyl chloride (1.7 ml), and the mixture was stirred at room temperature for 1.5 hours. Evaporation of the reaction solution gave a residue, which was then chromatographed on silica gel column (eluent: methylene chloride) to give methyl 4-(chloromethyl)cinnamate (2.57 g).

$^1$H-NMR (CDCl$_3$)δ:

3.80(3H, s), 4.60(2H, s), 6.44(1H, d, J=15 Hz), 7.40(2H, m), 7.51(2H, m), 7.69(1H, d, J=15 Hz),

A mixture of bis[2-(4-chlorophenylsulfonylamino)ethyl]disulfide (1.2 g), tributylphosphine (0.65 ml) and 90% methanol (30 ml) was stirred under an argon atmosphere at room temperature for 30 minutes, and the reaction mixture was evaporated under reduced pressure. To the residue were added under an argon atmosphere potassium carbonate (1.3 g) and N,N-dimethylformamide (20 ml). Then, methyl 4-(chloromethyl)cinnamate (1 g) obtained above was added thereto, and the mixture was stirred at room temperature for 16 hours. To the reaction mixture was added ethyl acetate, and the mixture was washed twice with a saturated aqueous sodium chloride solution and dried over anhydrous magnesium sulfate. Evaporation of the solvent under reduced pressure gave methyl 4-[2-(4-chlorophenylsulfonylamino) ethylthiomethyl]cinnamate (Compound No. 64) (1.74 g).

m.p. 99–103° C.

EXAMPLE 10

Following a similar manner to that of Example 9 using ethyl 4-[2-(methylsulfonyloxy)ethyl]phenoxyacetate or ethyl 4-[3-(methylsulfonyloxy)propyl]phenoxyacetate, there were obtained the following compounds.

Ethyl 4-{2-[2-(phenylsulfonylamino)ethylthio] ethyl}phenoxyacetate (Compound No. 65)

$^1$H-NMR (CDCl$_3$)δ:

1.30(3H, t, J=7 Hz), 2.53(2H, t, J=6 Hz), 2.58(2H, m), 2.72(2H, m), 3.10(2H, brq, J=6 Hz), 4.26(2H, q, J=7 Hz), 4.60(2H, s), 5.00(1H, brs), 6.83(2H, m), 7.05(2H, m), 7.50(3H, m), 7.85(2H, m)

Ethyl 4-{2-[3-(phenylsulfonylamino)propylthio] ethyl}phenoxyacetate (Compound No. 66)

$^1$H-NMR (CDCl$_3$)δ:

1.30(3H, t, J=7 Hz), 1.76(2H, m), 2.35(2H, t, J=6 Hz), 2.59(4H, m), 3.10(2H, brs), 4. 25(2H, q, J=7 Hz), 4.60(2H, s), 4.98(1H, brs), 6.82(2H, m), 7.02(2H, 7.52 (3H, m), 7.85(2H, m)

EXAMPLE 11

To a mixture of ethyl 2,6-difluoro-4-[2-(phenylsulfonylamino)ethylthio]phenoxyacetate (1.5 g) and ethanol (12 ml) was added 10% sodium hydroxide (3 ml), and the mixture was stirred at room temperature for 30 minutes. The reaction mixture was made acidic with 3% hydrochloric acid and extracted with ethyl acetate. The ethyl acetate layer was washed with a saturated aqueous sodium chloride solution and dried over anhydrous magnesium sulfate. Evaporation of the solvent under reduced pressure gave 2,6-difluoro-4-[2-(phenylsulfonylamino)ethylthio] phenoxyacetic acid (Compound No. 67) (1.3 g).

m.p. 91–93° C.

In a similar manner, there were obtained the following compounds from the compounds obtained in Examples 1–6, and 8–10.

2,6-Difluoro-4-[2-(4-chlorophenylsulfonylamino) ethylthio]phenoxyacetic acid (Compound No. 68)

m.p. 97–98° C.

2,6-Difluoro-4-[2-(4-methylphenylsulfonylamino) ethylthio]phenoxyacetic acid (Compound No. 69)

m.p. 93–95° C.

2-Fluoro-4-[2-(phenylsulfonylamino)ethylthio] phenoxyacetic acid (Compound No. 70)

m.p. 122–126° C.

2-Fluoro-4-[2-(4-chlorophenylsulfonylamino)ethylthio] phenoxyacetic acid (Compound No. 71)

m.p. 111–113.5° C.

2-Fluoro-4-[2-(4-methylphenylsulfonylamino)ethylthio] phenoxyacetic acid (Compound No. 72)

m.p. 120.5–122.5° C.

4-[2-(Phenylsulfonylamino)ethylthio]phenoxyacetic acid (Compound No. 73)

m.p. 156–159° C.

4-[2-(4-Chlorophenylsulfonylamino)ethylthio] phenoxyacetic acid (Compound No. 74)

m.p. 142.5–144° C.

4-[2-(4-Methylphenylsulfonylamino)ethylthio] phenoxyacetic acid (Compound No. 75)

m.p. 152.8–155.1° C.

4-[2-(4-Methoxyphenylsulfonylamino)ethylthio] phenoxyacetic acid (Compound No. 76)

m.p. 128.7–130.9° C.

4-[2-(4-Fluorophenylsulfonylamino)ethylthio] phenoxyacetic acid (Compound No. 77)

m.p. 150.5–153.5° C.

4-[2-(4-Bromophenylsulfonylamino)ethylthio] phenoxyacetic acid (Compound No. 78)

m.p. 151.9–153.4° C.

4-[2-(2,5-Dichlorophenylsulfonylamino)ethylthio] phenoxyacetic acid (Compound No. 79)

m.p. 143.5–145.9° C.

4-[2-(2,4,5-Trichlorophenylsulfonylamino)ethylthio] phenoxyacetic acid (Compound No. 80)

m.p. 125.4–127.2° C.

4-[2-(2,3,4,5,6-Pentafluorophenylsulfonylamino) ethylthio]phenoxyacetic acid (Compound No. 81)

m.p. 113.5–116.3° C.

4-[2-(2,4,6-Trimethylphenylsulfonylamino)ethylthio] phenoxyacetic acid (Compound No. 82)

m.p. 129.4–131.4° C.

4-[2-(2,4,6-Triisopropylphenylsulfonylamino)ethylthio] phenoxyacetic acid (Compound No. 83)

m.p. 180.5–183.5° C.

4-[2-(2-Naphthylsulfonylamino)ethylthio]phenoxyacetic acid (Compound No. 84)

m.p. 74–79.5° C.

4-[2-(4-Nitrophenylsulfonylamino)ethylthio] phenoxyacetic acid (Compound No. 85)

m.p. 160.4–162.5° C.

4-[2-(4-Chloro-3-nitrophenylsulfonylamino)ethylthio] phenoxyacetic acid (Compound No. 86)

m.p. 91.5–95.8° C.

Potassium 4-[2-(4-acetylaminophenylsulfonylamino) ethylthio]phenoxyacetate (Compound No. 87)

$^1$H-NMR (DMSO-d$_6$)δ:

2.07(3H, s), 2.5–2.8(4H, m), 4.11(2H, s), 6.69(2H, d, J=9 Hz), 7.09(2H, d, J=9 Hz), 7.3–7.6(4H, m)

4-[2-(3-Pyridylsulfonylamino)ethylthio]phenoxyacetic acid (Compound No. 88)

m.p. 163.2–165.1° C.

4-[2-(3,5-Dichloro-4-hydroxyphenylsulfonylamino) ethylthio]phenoxyacetic acid (Compound No. 89)

m.p. 125.3–129.4° C.

4-[2-(Phenylsulfonylamino)ethylsulfinyl]phenoxyacetic acid (Compound No. 90)

m.p. 182.5–183.5° C.

4-[2-(Phenylsulfonylamino)ethylsulfonyl]phenoxyacetic acid (Compound No. 91)

m.p. 156–158.5° C.

Sodium 4-[2-(phenylsulfonylamino)ethylthio]phenylacetate (Compound No. 92)
m.p. 157.5–159.5° C.

4-[2-(4-Chlorophenylsulfonylamino)ethylthio]phenylacetic acid (Compound No. 93)
m.p. 129–131° C.

4-[2-(4-Methylsulfonylamino)ethylthio]phenylacetic acid (Compound No. 94)
m.p. 95–97° C.

Sodium 4-[2-(phenylsulfonylamino)ethylthiomethyl]phenoxyacetate (Compound No. 95)
$^1$H-NMR (DMSO-$d_6$)δ:
2.38(2H, m), 2.80(2H, m), 3.50(2H, s), 4.09(2H, s), 6.70(2H, m), 7.05(2H, m), 7.33(3H, m), 7.60(2H, m)

4-[2-(4-Chlorophenylsulfonylamino)ethylthiomethyl]phenoxyacetic acid (Compound No. 96)
m.p. 123–124° C.

4-[2-(4-Chlorophenylsulfonylamino)ethylthiomethyl]cinnamic acid (Compound No. 97)
m.p. 173–174° C.

Sodium 4-{2-[(2-phenylsulfonylamino)ethylthio]ethyl}phenoxyacetate (Compound No. 98)
$^1$H-NMR (DMSO-$d_6$)δ:
2.40(2H, dd, J=6, 8 Hz), 2.60(4H, m), 2.80(2H, dd, J=6, 8 Hz), 4.08(2H, s), 6.70(2H, m), 7.00(2H, m), 7.85(3H, m), 7.62(2H, m)

Sodium 4-{2-[(2-phenylsulfonylamino)propylthio]ethyl}phenoxyacetate (Compound No. 99)
$^1$H-NMR (DMSO-$d_6$)δ:
1.65(2H, m), 2.35(4H, m), 2.75(2H, m), 4.06(2H, s), 6.70 (2H, m), 7.00 (2H, m), 7.33(3H, m), 7.60(2H, m)

3-{4-[2-(Phenylsulfonylamino)ethylthio]phenyl}propionic acid (Compound No. 100)
m.p. 146.2–148.1° C.

3-{4-[2-(2-naphthylsulfonylamino)ethylthio]phenyl}propionic acid (Compound No. 101)
m.p. 132.1–134.5° C.

3-{4-[2-(2,4,6-Triisopropylphenylsulfonylamino)ethylthio]phenyl}propionic acid (Compound No. 102)
m.p. 113.5–116.9° C.

3-{4-[2-(4-Nitrophenylsulfonylamino)ethylthio]phenyl}propionic acid (Compound No. 103)
m.p. 154–156.2° C.

3-{4-[2-(2,4,5-Trichlorophenylsulfonylamino)ethylthio]phenyl}propionic acid (Compound No. 104)
m.p. 123.4–126.6° C.

2-Fluoro-4-[2-(4-fluorophenylsulfonylamino)ethylthio]phenoxyacetic acid (Compound No. 105)
m.p. 126–128° C.

2-Fluoro-4-[2-(4-bromophenylsulfonylamino)ethylthio]phenoxyacetic acid (Compound No. 106)
m.p. 118.2–120.4° C.

2-Fluoro-4-[2-(4-methoxyphenylsulfonylamino)ethylthio]phenoxyacetic acid (Compound No. 107)
m.p. 144–146.1° C.

2-Fluoro-4-[2-(4-nitrophenylsulfonylamino)ethylthio]phenoxyacetic acid (Compound No. 108)
m.p. 140–142° C.

2-Fluoro-4-[2-(methylsulfonylamino)ethylthio]phenoxyacetic acid (Compound No. 109)
m.p. 88.8–91.3° C.

2-Fluoro-4-[2-(octylsulfonylamino)ethylthio]phenoxyacetic acid (Compound No. 110)
m.p. 107.6–109.3° C.

2-Fluoro-4-[2-(hexadecylsulfonylamino)ethylthio]phenoxyacetic acid (Compound No. 111)
m.p. 120.4–123.3° C.

4-[2-(4-Fluorophenylsulfonylamino)ethylthio]phenylacetic acid (Compound No. 112)
m.p. 102.8–105.6° C.

4-[2-(4-Bromophenylsulfonylamino)ethylthio]phenylacetic acid (Compound No. 113)
m.p. 126–129.6° C.

4-[2-(4-Methoxyphenylsulfonylamino)ethylthio]phenylacetic acid (Compound No. 114)
m.p. 84.5–87.4° C.

4-[2-(4-Nitrophenylsulfonylamino)ethylthio]phenylacetic acid (Compound No. 115)
m.p. 114.6–117.9° C.

4-[2-(Methylsulfonylamino)ethylthio]phenylacetic acid (Compound No. 116)
m.p. 108.3–111° C.

4-[2-(Octylsulfonylamino)ethylthio]phenylacetic acid (Compound No. 117)
m.p. 111.9–114.6° C.

4-[2-(Hexadecylsulfonylamino)ethylthio]phenylacetic acid (Compound No. 118)
m.p. 111.8–114.3° C.

2,6-Difluoro-4-[2-(4-fluorophenylsulfonylamino)ethylthio]phenoxyacetic acid (Compound No. 119)
m.p. 84.8–87.7° C.

2,6-Difluoro-4-[2-(4-bromophenylsulfonylamino)ethylthio]phenoxyacetic acid (Compound No. 120)
m.p. 113.4–116.5° C.

2,6-Difluoro-4-[2-(4-nitrophenylsulfonylamino)ethylthio]phenoxyacetic acid (Compound No. 121)
m.p. 115.6–119° C.

2,6-Difluoro-4-[2-(methylsulfonylamino)ethylthio]phenoxyacetic acid (Compound No. 122)
m.p. 117.8–121.5° C.

2,6-Difluoro-4-[2-(octylsulfonylamino)ethylthio]phenoxyacetic acid (Compound No. 123)
m.p. 98–101.3° C.

2,6-Difluoro-4-[2-(4-hexadecylsulfonylamino)ethylthio]phenoxyacetic acid (Compound No. 124)
m.p. 118.8–120.9° C.

2,6-Difluoro-4-[2-(4-methoxyphenylsulfonylamino)ethylthio]phenoxyacetic acid (Compound No. 125)
$^1$H-NMR (CDCl$_3$)δ:
2.9–3.2(4H, m), 3.87(3H, s), 4.78(2H, s), 5.2(1H, brs), 6.7–7.0(4H, m), 7.6–7.8(2H, m), 8.5(1H, brs)

4-[2-(4-Chlorophenylsulfonylamino)ethylsulfinyl]-2,6-difluorophenoxyacetic acid (Compound No. 126)
m.p. 129–129.5° C.

4-[2-(4-Chlorophenylsulfonylamino)ethylsulfonyl]-2,6-difluorophenoxyacetic acid (Compound No. 127)
m.p. 163–163.5° C.

EXAMPLE 12

To a mixture of 2,6-difluorophenol (25 g), potassium carbonate (39.5 g) and acetone (100 ml) was added dropwise with stirring at room temperature a solution of methyl bromoacetate (17.8 ml) in acetone (100 ml). After stirring at room temperature overnight, the reaction mixture was taken up in a mixture of conc. hydrochloric acid (40 ml) and ice water (500 ml), and extracted with ethyl acetate. The ethyl acetate layer was washed with a saturated aqueous sodium chloride solution and dried over anhydrous magnesium sulfate. Evaporation of the solvent under reduced pressure gave methyl 2,6-difluorophenoxyacetate (38 g) as a colorless oil.

$^1$H-NMR (CDCl$_3$)δ:
3.80(3H, s), 4.77(2H, s), 6.8–7.1(3H, m)

To a mixture of methyl 2,6-difluorophenoxyacetate (7.6 g) and methylene chloride (50 ml) was added dropwise chlorosulfonic acid (5.0 ml), and the reaction mixture was stirred at room temperature for 1.5 hours. Thionyl chloride (4.1 ml) was added to the reaction mixture, and the mixture was heated at reflux for 40 minutes. The reaction mixture, after cooling, was poured into ice water (200 ml), and the methylene chloride layer was washed successively with water and a saturated aqueous sodium chloride solution and dried over anhydrous magnesium sulfate. Evaporation of the solvent under reduced pressure gave methyl (2,6-difluoro-4-chlorosulfonyl)phenoxyacetate (11.1 g) as a colorless oil.

$^1$H-NMR (CDCl$_3$)δ:

3.80(3H, s), 4.96(2H, s), 7.63(2H, m)

To a mixture of methyl (2,6-difluoro-4-chlorosulfonyl) phenoxyacetate (11.1 g), tin (powder, 15.3 g) and methanol (100 ml) was added dropwise with stirring at 50–60° C. conc. hydrochloric acid (25 ml), and the reaction mixture was heated at reflux with stirring for 2 hours. After cooling, the reaction mixture was poured into ice water (200 ml) with decanting the insolubles, and extracted with methylene chloride. The methylene chloride layer was washed with a saturated aqueous sodium chloride solution, and dried over anhydrous magnesium sulfate. Evaporation of the solvent under reduced pressure gave methyl (2,6-difluoro-4-mercapto)phenoxyacetate (8.0 g) as an yellow oil.

A mixture of methyl (2,6-difluoro-4-mercapto) phenoxyacetate (8.0 g), potassium carbonate (5.6 g) and acetone (20 ml) was stirred under an argon atmosphere at room temperature for 20 minutes. To the reaction mixture was added dropwise over 10 minutes period a solution of N-(2-chloroethyl)-4-chlorophenylsulfonamide (8.9 g) in acetone (30 ml), and the mixture was stirred at room temperature overnight. The reaction solution was poured into a mixture of conc. hydrochloric acid (8 ml) and ice water (200 ml), and extracted with ethyl acetate. The ethyl acetate layer was washed successively with water and a saturated aqueous sodium chloride solution and dried over anhydrous magnesium sulfate. The solvent was evaporated under reduced pressure, the residue was recrystallized from an aqueous methanol solution to give methyl 4-[2-(4-chlorophenylsulfonylamino)ethylthio]-2,6-difluorophenoxyacetate (Compound No. 128) (12.7 g).

m.p. 79.5–80.5° C.

EXAMPLE 13

To a mixture of ethyl 4-[2-(4-chlorophenylsulfonylamino) ethylthio]-2,6-difluorophenoxyacetate (0.46 g) and tetrahydrofuran (30 ml) was added under ice cooling lithium aluminum hydride (38 mg), and the mixture was stirred at room temperature for an hour. To the reaction mixture was added successively 10% aqueous sodium hydroxide solution (0.2 ml), ethyl acetate (30 ml) and anhydrous sodium sulfate (1 g), and the insolubles were removed by filtration. After evaporation of the filtrate under reduced pressure, the residue was chromatographed on silica gel column (eluent; ethyl acetate:hexane=1:1), and the desired fractions were collected and recrystallized from ethyl ether/isopropyl ether mixture to give 2-{4-[2-(4-chlorophenylsulfonylamino) ethylthio]-2,6-difluorophenoxy}ethanol (Compound No. 129).

m.p. 43.5–45° C.

EXAMPLE 14

To a mixture of 4-hydroxybenzaldehyde (6.1 g), potassium carbonate (13.8 g), sodium iodide (0.75 g) and N,N-dimethylformamide (110 ml) was added N-(ethoxycarbonylmethyl)-2-chloroacetamide (8.9 g), and the mixture was stirred at 80° C. for 30 minutes. The reaction mixture was poured into 3% hydrochloric acid and extracted with ethyl acetate. The ethyl acetate layer was washed successively with water and a saturated aqueous sodium chloride solution and dried over anhydrous magnesium sulfate. After evaporation of the solvent under reduced pressure, the residue was chromatographed on silica gel column (eluent; ethyl acetate), the desired fractions were collected and recrystallized from ethyl acetate/hexane to give N-(ethoxycarbonylmethyl)-2-(4-formylphenoxy) acetamide (4.09 g).

m.p. 94.5–95.5° C.

To a mixture of N-(ethoxycarbonylmethyl)-2-(4-formylphenoxy)acetamide (4.6 g) and ethanol (150 ml) was added under ice cooling sodim borohydride (0.25 g), and the mixture was stirred at room temperature for 30 minutes. To the reaction mixture was added 3% hydrochloric acid, and the mixture was extracted with ethyl acetate. The ethyl acetate layer was washed with a saturated aqueous sodium chloride solution and dried over anhydrous magnesium sulfate. Evaporation of the solvent under reduced pressure gave N-(ethoxycarbonylmethyl)-2-(4-hydroxymethylphenoxy)acetamide (4.03 g).

$^1$H-NMR (CDCl$_3$)δ:

1.29(3H, t, J=7 Hz), 1.72(1H, brs), 4.10(2H, d, J=5 Hz), 4.22(2H, q, J=7 Hz), 4.51(2H, s), 4.64(2H, s), 6.92(2H, m), 7.08(1H, brs), 7.32(2H, m)

A mixture of N-(ethoxycarbonylmethyl)-2-(4-hydroxymethylphenoxy)acetamide (3.96 g), triphenylphosphine (3.88 g), carbon tetrachloride (10 ml) and methylene chloride (20 ml) was heated at reflux for 1.5 hours. The reaction mixture was evaporated under reduced pressure, and ethyl acetate was added to the residue. After removal of the insolubles by filtration, the filtrate was chromatographed on silica gel column (eluent; ethyl acetate), and the desired fractions were collected and recrystallized from ethyl acetate/ether to give N-(ethoxycarbonylmethyl)-2-(4-chloromethylphenoxy)acetamide (2.8 g).

m.p. 88.5–90.5° C.

A mixture of N-(ethoxycarbonylmethyl)-2-(4-chloromethylphenoxy)acetamide (2.5 g), 2-(4-chlorophenylsulfonylamino)ethanethiol (3.36 g), potassium carbonate (2.5 g) and N,N-dimethylformamide (50 ml) was stirred at room temperature for 3 days. The reaction mixture was poured into 3% hydrochloric acid and extracted with ethyl acetate. The ethyl acetate layer was washed successively with water and a saturated aqueous sodium chloride solution and dried over anhydrous magnesium sulfate. After evaporation of the solvent under reduced pressure, the residue was chromatographed on silica gel column (eluent; ethyl acetate:hexane=1:2–1:0), and the desired fractions were collected and recrystallized from ether to give N-(ethoxycarbonylmethyl)-4-[2-(4-chlorophenylsulfonylamino)ethylthiomethyl]-2,6-difluorophenoxyacetamide (Compound No. 130).

m.p. 88.5–89.5 ° C.

The compound obtained in Example 14 was treated with an aqueous sodium hydroxide solution to give N-(carboxymethyl)-4-[2-(4-chlorophenylsulfonylamino) ethylthiomethyl]-2,6-difluorophenoxyacetamide (Compound No. 131).

m.p. 140–140.5° C.

EXAMPLE 15

Methyl 4-[2-(4-chlorophenylsulfonylamino)ethylthio]-2, 6-difluorophenoxyacetate (1 g) was added to methanol (50 ml) saturated with ammonia gas, and the mixture was stirred at room temperature for 3 days. The reaction mixture was evaporated under reduced pressure, and the residue was recrystallized from methanol to give 4-[2-(4-chlorophenylsulfonylamino)ethylthio]-2,6-difluorophenoxyacetamide (Compound No. 132).

m.p. 162–163.5° C.

Following a similar manner to that of Example 15, there were obtained the following compounds.

N,N-Dimethyl-4-[2-(4-chlorophenylsulfonylamino)ethylthio]-2,6-difluorophenoxyacetamide (Compound No. 133)

m.p. 136.3–137.7° C.

N-Hydroxy-4-[2-(4-chlorophenylsulfonylamino)ethylthio]-2,6-difluorophenoxyacetamide (Compound No. 134).

m.p. 132.2–133.7° C.

4-[2-(4-Chlorophenylsulfonylamino)ethylthio]-2-fluorophenoxyacetamide (Compound No. 135)

m.p. 105.8–107.9° C.

N,N-Dimethyl-4-[2-(4-chlorophenylsulfonylamino)ethylthio]-2-fluorophenoxyacetamide (Compound No. 136)

m.p. 142.8–144.1° C.

N-Hydroxy-4-[2-(4-chlorophenylsulfonylamino)ethylthio]-2-fluorophenoxyacetamide (Compound No. 137)

$^1$H-NMR δ: (acetone $d_6$)
2.9–3.3(2H, m), 4.73(2H, s), 6.9(1H, brs), 7.0–7.2(3H, m), 7.58(2H, d, J=8.79 Hz), 7.86(2H, d, J=8.79 Hz), 8.9(1H, brs), 10.4(1H, brs)

4-[2-(4-Chlorophenylsulfonylamino)ethylthio]phenylacetamide (Compound No. 138)

m.p. 195.3–197.2° C.

4-[2-(Phenylsulfonylamino)ethylthio]-2,6-difluorophenoxyacetamide (Compound No. 139)

m.p. 117.6–120.8° C.

N,N-Dimethyl-4-[2-(phenylsulfonylamino)ethylthio]-2,6-difluorophenoxyacetamide (Compound No.140)

$^1$H-NMR δ: (acetone $d_6$)
2.91(3H, s), 3.0–3.2(4H, m), 3.09(3H, s), 4.91(2H, s), 6.8–7.1(2H, m), 6.9(1H, brs), 7.5–7.7(3H, m), 7.8–7.9 (2H, m)

N-Hydroxy-4-[2-(phenylsulfonylamino)ethylthio]-2,6-difluorophenoxyacetamide (Compound No. 141)

$^1$H-NMR δ: (acetone $d_6$)
3.0–3.2(4H, m), 4.69(2H, s), 6.9(1H, brs), 6.9–7.1 (2H, m), 7.5–7.7(3H, m), 7.8–8.0(2H, m), 8.7(1H, brs), 10.5(1H, brs)

4-[2-(Phenylsulfonylamino)ethylthio]-2-fluorophenoxyacetamide (Compound No. 142)

m.p. 108.9–110.4° C.

N,N-Dimethyl-4-[2-(phenylsulfonylamino)ethylthio]-2-fluorophenoxyacetamide (Compound No. 143)

m.p. 104–105.4° C.

N-Hydroxy-4-[2-(phenylsulfonylamino)ethylthio]-2-fluorophenoxyacetamide (Compound No.144)

$^1$H-NMR δ: (acetone $d_6$)
2.9–3.4(4H, m), 4.72(2H, s), 6.8(1H, brs), 6.9–7.2(3H, m), 7.5–7.7(3H, m), 7.7–8.0(2H, m), 8.8(1H, brs), 10.5(1H, brs)

4-[2-(phenylsulfonylamino)ethylthio]phenylacetamide (Compound No. 145)

m.p. 152.8–155.9° C.

EXAMPLE 16

For the purpose of illustrating the usefulness of the compound produced by the above-mentioned method, the potentiation action of the electrophysiological response of non-NMDA receptors was measured, about the typical compounds shown in table 1.

Method of Measure

By use of an improved method of Masu's *Xenopus oocyte* expression system [Nature 329,836 (1987)] an electrophysiological analysis was conducted.

(1) Preparation of poly(A)$^+$RNA isolated from a rat hippocampus.

A hippocampus region was isolated from a rat and homogenized in the presence of guanidine isocyanate and total RNA was extracted from the hippocampus by means of the ultracentrifugating method utilizing cesium chloride. Poly(A)$^+$RNA was refined from the obtained RNA by use of oligo dT cellulose column.

(2) Expression of protein in *Xenopus oocytes*

50 nl of the poly(A)$^+$RNA (1 μg/μl) isolated was injected into an oocyte by a micromanipulator and the oocytes were cultured in a Barth's medium (88 mM NaCl, 1 mM KCl, 2.4 mM NaHCO$_3$, 0.3 mM Ca(NO$_3$)$_2$, 0.41 mM CaCl$_2$, 0.82 mM MgSO$_4$, 10 μg/ml sodium penicillin, 10 μg/ml streptomycin sulfate, and 15 mM HEPES) at 19° C. for three to four days and used for measurement.

(3) Electrophysiological and pharmacological experiment by two-electrodes voltage clamp method.

The above-mentioned oocyte was set in a chamber under perfusion of frog Ringer's solution (120 mM NaCl, 2 mM KCl, 1.8 mM CaCl$_2$, and 5 mM HEPES, pH 7.4) and microelectrodes were inserted into oocytes and the membrane potential was fixed at −70 mV. Subsequently, another frog Ringer's solution in which AMPA (100 μM) or kainate (KA) (100 μM) both of which are agonists for non-NMDA receptors was dissolved was substituted for the original Ringer's solution and then an inward membrane current was measured. From the fact this response (inward membrane current) is inhibited by CNQX (1 μM) which is an antagonist for non-NMDA receptors it is presumed that this response may be caused by non-NMDA receptors.

Then a comparison was made between membrane current① elicited under perfusion of frog Ringer's solution in which the compound of the present invention was dissolved in DMSO solution and furthermore 100 μM AMPA or 100 μM kainic acid was added until a final concentration of 50 μM, and membrane current② elicited under perfusion of frog Ringer's solution as a control comprising 100 μM AMPA or 100 μM kainic acid and then a potent potentiation of current was observed in this measurement. The results were shown in table 1.

In this experiment anilacetum was used as a control medicament and this medicament is known as a potentiator for non-NMDA receptors. [J. Physiology 424, 533–543 (1990)]

It was presumed that the compound of the invention can potentiate membrane current elicited with kainic acid and AMPA, and affect non-NMDA receptors as shown in table 1. (definitely active, especially with compound 139). Contrarily, anilacetum, with an addition of only 50 μM, does not potentiate membrane current elicited by AMPA or kainic acid, and also, with an addition of 1 mM, 20 times in concentration, does not affect a response elicited by kainic acid, but, with an addition of the same amount doubles a response elicited by AMPA. This illustration showed that the compound of the invention have a far more strong ability to potentiate the activity of non-NMDA receptors than that of anilacetum which is a conventional potentiator for non-NMDA receptors.

The compound of this invention may inhibit or may not affect membrane current elicited under perfusion of frog Ringer's solution in which NMDA being an agonist for NMDA receptors was dissolved until a final concentration of 100 μM. Accordingly the compound of the invention has proved to be a potentiator for non-NMDA receptors.

And, in frog Ringer's solution used to administrate NMDA 5 mM $BaCl_2$ was substituted for 1.8 mM $CaCl_2$. In the above-mentioned system inward membrane current was observed under perfusion of frog Ringer's solution in which the compound of the invention was dissolved solely. This response (inward membrane current) was inhibited by CNQX (1 μM) which is an antagonist for non-NMDA receptors but was not inhibited by an antagonist MK-801(1 μM) for NMDA receptors. This fact has indicated that the compound of the invention can act as an agonist for non-NMDA receptors.

As a result of the said experiment the compound of the invention is expected to activate, as a potentiator for non-NMDA receptors, glutamate receptors which exist in brains in which deterioration of the activity is reported because of neuronal disorders, and to become an effective agonist for glutamate receptors to make it possible to recover the normal action of the neurotransmission.

TABLE 1

Potentiation (relative values with a control as 1)

| compound number | kainic acid | AMPA |
|---|---|---|
| 68 | 1.6 | 1.5 |
| 106 | 1.5 | 1.4 |
| 128 | 1.6 | 1.5 |
| 139 | 2.8 | 23.2 |
| 142 | 1.5 | 1.6 |
| 143 | 1.6 | 1.4 |
| 145 | 1.5 | 1.3 |
| anilacetum | 1 | 1 |

The table 1 shows the rates at which the compounds of the invention potentiates the membrane current elicited by AMPA or kainic acid. Namely, poly(A)$^+$RNA isolated from rat hippocampus was injected into a *Xenopus oocyte* and cultured for three days and then, the expression of glutamate receptors was observed in the oocytes. The membrane potential was fixed at −70 mV. The response was defined as one which was generated on the specimen under perfusion of frog Ringer's solution in which AMPA or kainic acid both of which are agonists for non-NMDA receptors was dissolved until a final concentration of 100 μM. The responses are shown as relative values which were measured on the oocytes under perfusion of frog Ringer's solution in which the compound of the invention and anilacetum which is a potentiator for non-NMDA receptors were dissolved until a concentration of 50 μM with AMPA or kainic acid. The compound of the present invention can activate the above response by non-NMDA receptors and the compound 139, among the invented compounds, has shown especially strong action.

The compound numbers shown in table 1 represent the same compound numbers as in the above examples.

The compound of the invention can be utilized as doses for oral, hypodermic, intramuscular, intravenous and suppository administrations in a wide range of forms of the pharmaceutical composition such as powder, granule, tablet, glycocalyx and capsule which can be produced by the conventional pharmaceutical technology.

In production of the above-mentioned forms of the pharmaceutical compositions such ordinary additives as extending, bonding, disintegrating, pH regulating and resolving agents can be employed.

The unit dosage of the compound of the invention to the subjects in need of treatment may varies depending upon the age, the kind and the state of disease and an amount of 1 to 5000 mg of the compound daily can be divided into 1 to several sub-doses and administrated.

[POSSIBILITY OF INDUSTRIAL UTILIZATION]

This invention can provide excellent medical substances capable of potentiating the responses of glutamate receptors comprising a sulfonamide derivertive or a pharmaceutically acceptable salt thereof as an effective ingredient.

We claim:

1. A method comprising administering a sulfonamide derivative to a patient requiring activation of glutamate receptors, the sulfonamide derivative represented by the formula

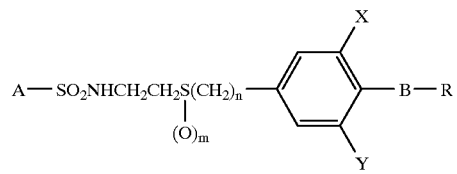

wherein A is a napthyl group, a pyridyl group, a phenyl group, a phenyl group substituted by 1 to 5 members selected from the group consisting of a halogen atom, an alkyl group having 1 to 40 carbon atoms, an alkoxy group having 1 to 4 carbon atoms, a nitro group, and an acetamido group, or an alkyl group having 1 to 20 carbon atoms; B is an alkylene group having 1 to 3 carbon atoms, a group of —OCH$_2$— or a group of —CH=CH—; X and Y are the same or different, and are each a hydrogen atom or a fluorine atom; R is a carboxy group, an alkoxycarbonyl group having 2 to 5 carbon atoms, a hydroxymethyl group or a group of

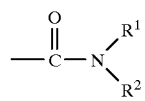

wherein $R_1$ is a hydrogen atom or an alkyl group having 1 to 3 carbon atoms; and $R_2$ is a hydrogen atom, a hydroxyl group, an alkyl group having 1 to 3 carbon atoms, a carboxymethyl group or an alkoxycarbonylmethyl group having 3 to 6 carbon atoms; m is an integer from 0 to 2; and n is an integer from 0 to 3, or an pharmaceutically acceptable salt thereof, as an effective ingredient.

2. A method comprising administering a sulfonamide derivative to a patient requiring activation of glutamate receptors, the sulfonamide derivative represented by the formula

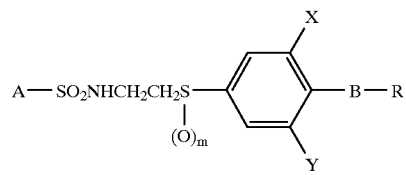

wherein A is a phenyl group substituted by 1 to 5 members selected from the group consisting of a halogen atom, an alkyl group having 1 to 4 carbon atoms, an alkoxy group having 1 to 4 carbon atoms, a nitro group and an acetamido group; B is an alkylene group having 1 to 3 carbon atoms or a group of —OCH$_2$—; X and Y are the same or different, and are each a hydrogen atom or a fluorine atom; R is a carboxy group or an alkoxycarbonyl group having 2 to 4 carbon atoms; and m is an integer from 0 to 2, or a pharmaceutically acceptable salt thereof, as an effective ingredient.

3. A method comprising administering a sulfonamide derivative to a patient requiring activation of glutamate receptors, the sulfonamide derivative represented by the formula

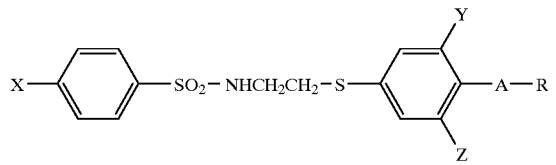

wherein X, Y and Z are the same or different, and are each a hydrogen atom or a halogen atom, wherein A is a methylene group or a group represented by the formula —OCH$_2$—, wherein R is carboxy group, an alkoxycarbonyl group having 2 to 5 carbon atoms, or

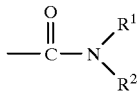

wherein $R^1$ is a hydrogen atom or an alkyl group having 1 to 3 carbon atoms, and $R^2$ is a hydrogen atom, a hydroxyl group, an alkyl group having 1 to 3 carbon atoms, or a pharmaceutically acceptable salt thereof, as an effective ingredient.

* * * * *